US008252249B2

(12) United States Patent
Ogawa

(10) Patent No.: US 8,252,249 B2
(45) Date of Patent: Aug. 28, 2012

(54) BIOCHEMICAL CHIP AND PRODUCTION METHOD THEREOF

(76) Inventor: Kazufumi Ogawa, Tokushima (JP)

( * ) Notice: Subject to any disclaimer, the term of this patent is extended or adjusted under 35 U.S.C. 154(b) by 1347 days.

(21) Appl. No.: 11/783,892

(22) Filed: Apr. 12, 2007

(65) Prior Publication Data

US 2007/0224082 A1 Sep. 27, 2007

(51) Int. Cl.
*G01N 1/00* (2006.01)
*G01N 33/48* (2006.01)

(52) U.S. Cl. ........ 422/503; 422/68.1; 422/501; 422/502

(58) Field of Classification Search ................. 422/68.1, 422/501-503
See application file for complete search history.

(56) References Cited

U.S. PATENT DOCUMENTS

| | | | | |
|---|---|---|---|---|
| 5,443,890 | A * | 8/1995 | Ohman | 428/167 |
| 6,054,190 | A * | 4/2000 | Ogawa et al. | 427/510 |
| 6,709,559 | B2 * | 3/2004 | Sundberg et al. | 204/604 |
| 2002/0041831 | A1 * | 4/2002 | Battrell et al. | 422/100 |
| 2003/0138941 | A1 * | 7/2003 | Gong et al. | 435/287.2 |
| 2004/0099310 | A1 * | 5/2004 | Andersson | 137/240 |
| 2006/0008678 | A1 * | 1/2006 | Fukushima et al. | 428/704 |
| 2006/0024504 | A1 * | 2/2006 | Nelson et al. | 428/409 |
| 2006/0171846 | A1 * | 8/2006 | Marr et al. | 422/82.11 |

FOREIGN PATENT DOCUMENTS

| | | | |
|---|---|---|---|
| EP | 1514596 | A2 * | 3/2005 |
| JP | 2005-106814 | | 4/2005 |
| JP | 2007-33167 | | 2/2007 |
| WO | 2004/067444 | A1 | 8/2004 |

OTHER PUBLICATIONS http://www.vp-scientific.com/hydrophobic_coating.htm.*
JPO; Office Action in related foreign application JP2005-215387; mailed Jun. 21, 2010.

* cited by examiner

*Primary Examiner* — In Suk Bullock
*Assistant Examiner* — Paul Hyun
(74) *Attorney, Agent, or Firm* — Maschoff Gilmore & Israelsen

(57) ABSTRACT

A biochemical chip in which at least the inner surface of a flow path is covered with a chemisorption monomolecular film having arbitrary surface energy, and the method includes: a step for pre-forming a chemisorption monomolecular film having arbitrary surface energy on the inner surfaces of flow path parts of first and second members which are processed to have flow paths; and a step for facing and bonding the first and second members.

17 Claims, 2 Drawing Sheets

BIOCHEMICAL CHIP AND PRODUCTION METHOD THEREOF

BACKGROUND

1. Technical Field

The present invention relates to a biochemical chip in which surface energy of a flow path is arbitrarily controlled, and a production method thereof.

More particularly, the present invention relates to a biochemical chip produced by facing and bonding a pair of biochemical chip substrates processed to have a fine flow path or hole on the surface thereof, in which the flow rate of a poured liquid is controlled by pre-covering the inner surface of the flow path with a chemisorption monomolecular film having arbitrary surface energy without damaging the flow path or hole, and to a production method thereof. In addition, the biochemical chip includes a chemical chip, a biochip, a biochemical electrophoresis chip, a biochemical reactor, a biochemical fluidic system, a DNA chip and the like, which are used for a chemical experiment, a bio-experiment, medical diagnosis and the like.

2. Related Art

The following production method of a biochemical chip has been publicly known, that is, a method for pouring a fine particle or the like into a flow path to control the flow rate in the flow path in advance, and facing and bonding a pair of members using an instantaneous adhesive or an optical curing adhesive.

However, as for the conventional biochemical chip, when the fine particle or the like is poured into the flow path so as to bond a facing pair of members, it has been difficult to bond the members without damaging the fine hole and groove, that is, without covering those by an adhesive, and without having gaps.

An objective of the present invention is to provide a biochemical chip in which the flow rate of a liquid in the flow path is controlled without taking any flow rate controlling members into the flow path.

SUMMARY

An advantage of some aspects of the invention is the provision of a biochemical chip in which at least the inner surface of a flow path is covered with an arbitrary chemisorption monomolecular film having arbitrary surface energy, and includes: a step for pre-forming a chemisorption monomolecular film having arbitrary surface energy on the inner surfaces of flow path parts of first and second members which are processed to have flow paths; and a step for facing and bonding the first and second members.

In this case, if the surface energy of the monomolecular film is controlled to have an arbitrary value of 2 to 70 mN/m, the flow rate of the most liquid can be controlled, so that it is preferable.

Further, if the chemisorption monomolecular film is formed with one of silane compounds or a mixture of a plurality of compounds which have a fluorocarbon group and a hydrocarbon group, it is preferable to control the surface energy.

Further, if the inner surface of the flow path is selectively covered with a plurality of chemisorption monomolecular films having arbitrarily surface energy, the flow rate of a liquid in one chemical chip can be partially controlled, so that it is preferable.

Further, at this time, if the chemical adsorbed monomolecular film is formed with a mixed monomolecular film having a fluorocarbon group and a hydrocarbon group, it is preferable to control the surface energy of the flow path.

Further, the monomolecular film can be efficiently formed by using: a step for contacting and reacting a member with a chemisorption liquid produced by mixing a non-aqueous organic solvent with a chlorosilane compound containing the fluorocarbon group and the hydrocarbon group or a chlorosilane compound containing a hydroxyl group after forming the film, and forming first and second members having a chemisorption monomolecular film containing the fluorocarbon group and the hydrocarbon group; or a step for contacting and reacting a member with a chemisorption liquid produced by mixing a non-aqueous organic solvent with an alkoxysilane compound containing the fluorocarbon group and the hydrocarbon group or an alkoxysilane compound containing a hydroxyl group after forming the film and a silanol condensed catalyst, and forming first and second members having a chemisorption monomolecular film containing the fluorocarbon group and the hydrocarbon group.

As described above, the present invention has the effect to provide a biochemical chip having high characteristics with low cost, in which the flow rate of a liquid in a flow path is controlled without taking any flow rate controlling members into the flow path.

BRIEF DESCRIPTION OF THE DRAWINGS

FIG. 1 is a schematic cross-sectional view for explaining a process for bonding a pair of glass biochemical chip substrates in Example 1 of the present invention, where the process is expanded to the molecular level.

DESCRIPTION OF EXEMPLARY EMBODIMENTS

Figure 1A:
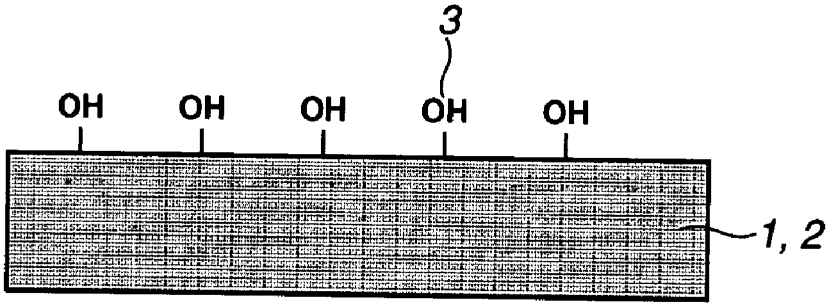
FIG. 1A is a view of the surface of a first glass substrate before the reaction.

The present invention is to produce and provide a biochemical chip in which the inner surface of a flow path is covered with an chemisorption monomolecular film having arbitrary surface energy for at least controlling flow rate, and the method for producing the biochemical chip includes: a step for pre-forming an chemisorption monomolecular film having arbitrary surface energy on the inner surfaces of flow path parts of first and second members which are processed to have flow paths; and a step for facing and bonding the first and second members.

Therefore, by using the method of the present invention, a biochemical chip having high characteristics can be provided with a low cost, where the flow rate of a liquid in a flow path is comparatively easily controlled by surface-modifying the inner surface of the flow path without taking any flow rate controlling members into the flow path.

Hereinafter, the present invention will be concretely described with Examples. However, the present invention is not limited to these examples. The present invention can be applied to any flow paths having a fine structure in a micron level.

In addition, the biochemical chip according to the present invention includes a chemical chip, a biochemical electrophoresis chip, a biochemical reactor, a biochemical fluidic system, a DNA chip and the like, which are used for a chemical experiment, a bio-experiment, medical diagnosis and the like. However, the present invention will be described using a chemical chip as a representative example.

Example 1

First, the glass biochemical chip substrates 1 and 2 used for a chemical chip was prepared, where one pair of flow paths were processed on the each substrate. One substrate had the flow path having the width of 5 microns and the depth of 5 microns and another substrate had the flow path having the width of 5 microns and the depth of 1 micron (a plastic substrate such as an acrylic resin or the like might be used, and when the plastic substrate was used, it could be used like the glass substrate by thinly oxidizing the surface by corona treatment or the like so as to have hydrophilicity). Then, the substrates 1 and 2 were well washed and dried after selectively forming resist films so as to expose flow path parts. Then, the chemisorption liquid was prepared by the steps of: weighing 99 w.t. % of chemicals including a function capable of decreasing the surface energy to a functional part as a chemical adsorbent, for example, chemicals including the fluorocarbon group at one end and an alkoxyl group at another end as the function capable of decreasing the surface energy, that is, for example, the chemicals shown in the following formula (1); weighing 1 w.t. % of, for example, dibutyl-tin-acetylacetonate as the silanol condensing catalyst; and solving the above-described weighed chemical materials in a silicone solvent, for example, a hexamethyldisiloxane solvent so as to have the total concentration of about 1 w.t. % (the concentration of the chemical adsorbent was preferably about 0.5 to 3%).

[Formula 1]

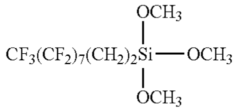

The chemisorption liquid was coated on the surfaces of the glass substrates 1 and 2, and reacted at a normal atmosphere (a relative humidity was 45%) for 2 hours. At this time, since many hydroxyl groups 3 were contained on the surfaces of the glass substrates 1 and 2 (FIG. 1A), a —$Si(OCH_3)$ group of the chemical adsorbent and the hydroxyl groups 2 were dealcoholation-reacted (in this case, de$CH_3OH$-reacted) under the existence of the silanol condensing catalyst, so as to form a bond shown in the following formula (2). Thereby, a chemical adsorbed film 4 containing the fluorocarbon group was formed to have the film thickness of about 1 nm, where the film 4 was chemically bonded to the portions which were exposed having no resists on the surfaces of the glass substrates 1 and 2.

Figure 1B:
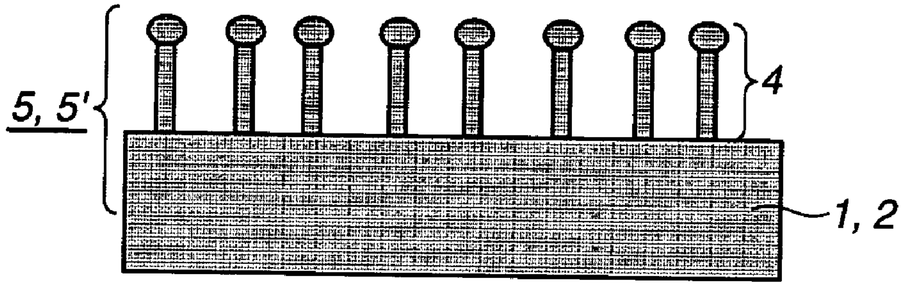
FIG. 1B is a view after forming a monomolecular film containing a fluorocarbon group.
Figure 1B:
Figure 1C:
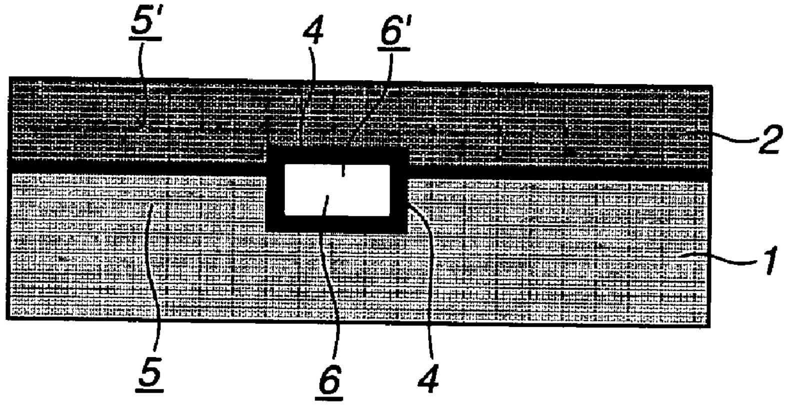
FIG. 1C is a cross-sectional view of a glass biochemical chip in which the first and second glass substrates, which is formed with a monomolecular film, are bonded.

Then, the resists were removed and the glass substrates were washed with a chlorine based solvent such as chloroform or the like, so that a first and second glass biochemical chip substrates 5 and 5' selectively covered with the chemisorption monomolecular film, which had the reactive fluorocarbon group, on the surface thereof could be produced (FIG. 1B).

[Formula 2]

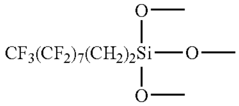

Finally, the two substrates were faced to be bonded, so that a biochemical chip covered with the chemisorption film 4 based on fluorocarbon, in which the surface energy of the flow paths 6 and 6' was 4 mN/m, could be produced (FIG. 1B).

In addition, since the monomolecular film formed by the above-described treatment had the film thickness in a nanometer level and was remarkably thin, the thickness of the glass was not changed, and the flow path and hole which were pre-processed were not damaged. Further, when the surface energy is going to have much more, the adsorbent capable of giving many hydroxyl groups to the surface, for example, tetramethoxysilane, which was as a silane compound having the hydroxyl group after forming the film, could be used, so as to control the surface energy to have about 70 mN/m.

Further, in this example, the chemicals shown in the chemical formula (1) was used. However, the chemicals to be used could be changed, or used by mixing with other chemicals. Thus, the surface energy on the inner surface of the flow path could be freely controlled within the range of 2 to 70, and thus, the flow rate could be controlled.

Example 2

On the other hand, a chlorosilane-based chemical adsorbent (MFS-17) shown in the following chemical formula (3) was used instead of the chemicals shown in the chemical formula (1).

[Formula 3]

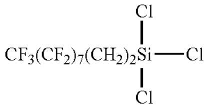

Even though the catalyst was not used, the chemical adsorbent was dehydrochlorination-reacted with the substrate surface so as to form the bond shown in the above-described chemical formula (2), and the chemisorption monomolecular film 4 containing the fluorocarbon group was formed having the film thickness of about 1 nm, where the film 4 was similar to that of Example 1 chemically bonded to the parts which were exposed having no resists of the surfaces of the glass substrate 1 and 2.

Figure 2:
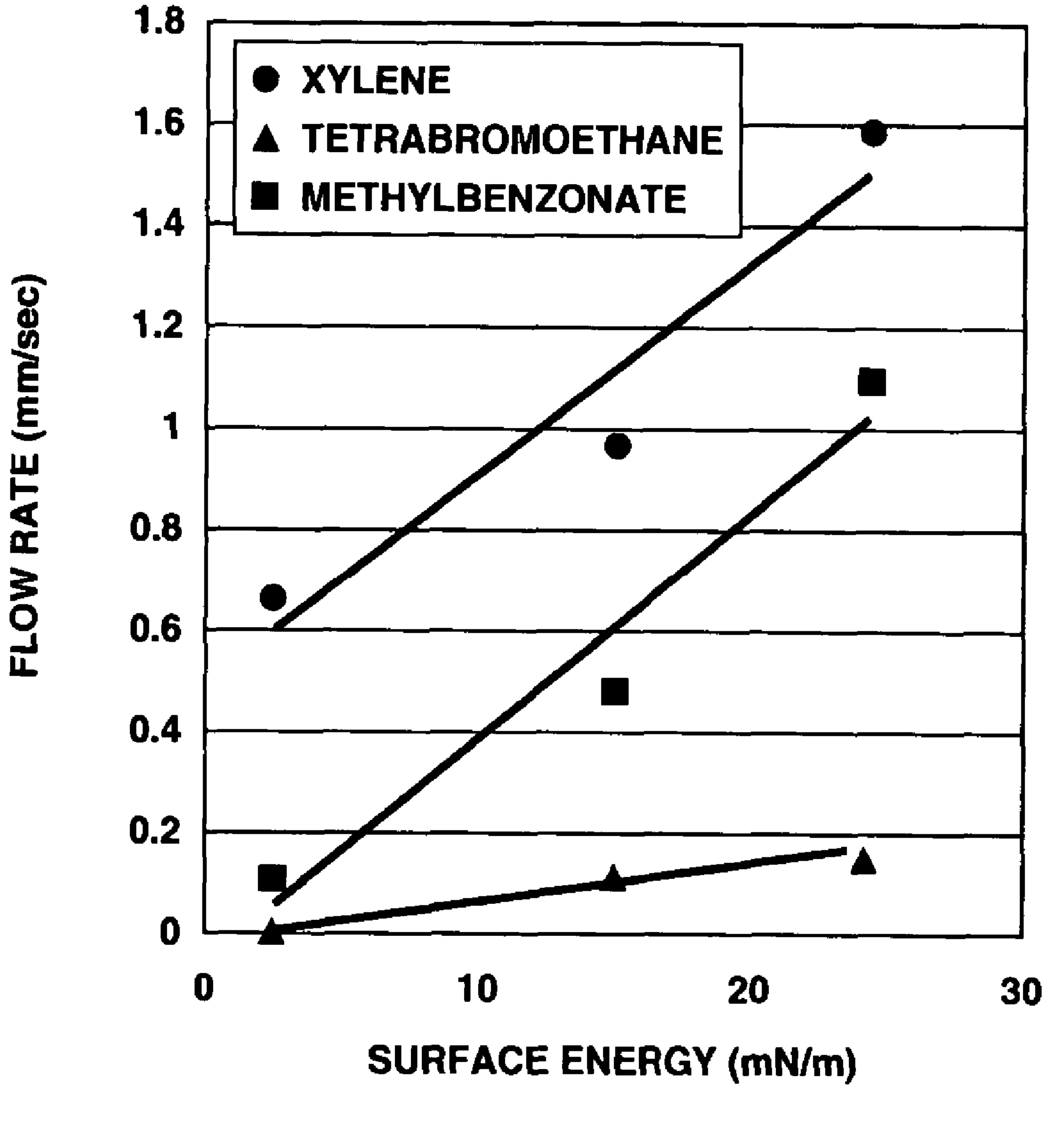
FIG. 2 is a graph showing the relationship between flow rate and surface energy when the flow rate has the width of 5 microns and the depth of 5 microns.

Here, the relationship between the surface energy and the adsorbent used for forming the film was partially shown in Table 1, where the adsorbent was used when the flow path had the width of 5 microns and the depth of 5 microns. Further, the relationship between the surface energy of the flow path and the flow rate of the poured liquid was partially shown in Table 2. Furthermore, a typical graph plotting the relationship between the flow rate and the surface energy was shown in FIG. 2. In addition, the surface energy was measured using Zisman Plot.

As a result of this, it was clear that the flow rate of the solution could be controlled by forming a film having different surface energy on the inner wall of the flow path.

In this case, MFS-17 shows $CF_3(CF_2)_7(CH_2)_2SiCl_3$, LS-120 shows $CH_3(CH_2)_{17}SiCl_3$, and LS-6495 shows $CH_3CH_2SiCl_3$.

TABLE 1

| Chemicals to be used | Surface Energy of Monomolecular film (mN/m) |
|---|---|
| MFS-17 | 4.4 |
| MFS-17 + LS-120 (1:1) | 2.6 |
| MFS-17 + LS-6495 (1:9) | 15.0 |
| LS-6495 | 20.6 |
| LS-120 | 24.4 |

TABLE 2

| Monomolecular Film (Surface Energy: mN/m) | Poured Liquid (Rate: mm/sec) Xylene | Methyl-benzoate | Tetrabromoethane |
|---|---|---|---|
| MFS-17 + LS-120(1:1) 2.6 | 0.665 | 0.106 | Not flow |
| MFS-17 + LS-6495(1:9) 15.0 | 0.968 | 0.482 | 0.119 |
| LS-120 24.4 | 1.586 | 0.460 | 0.150 |

In addition, in the above-described Example 1, $CF_3(CF_2)_7(CH_2)_2SiCl_3$ was used as the fluorocarbon-based chemical adsorbent. However, in addition to the above-described adsorbents, the chemicals shown in the following (1) to (12) including a hydrocarbon group could be used.

(1) $CF_3CH_2O(CH_2)_{15}SiCl_3$
(2) $CF_3(CH_2)_3Si(CH_3)_2(CH_2)_{15}SiCl_3$
(3) $CF_3(CF_2)_5(CH_2)_2Si(CH_3)_2(CH_2)_9SiCl_3$
(4) $CF_3(CF_2)_7(CH_2)_2Si(CH_3)_2(CH_2)_9SiCl_3$
(5) $CF_3COO(CH_2)_{15}SiCl_3$
(6) $CF_3(CF_2)_5(CH_2)_2SiCl_3$
(7) $CH_3CH_2O(CH_2)_{15}SiCl_3$
(8) $CH_3(CH_2)_3Si(CH_3)_2(CH_2)_{15}SiCl_3$
(9) $CH_3(CH_2)_5Si(CH_3)_2(CH_2)_9SiCl_3$
(10) $CH_3(CH_2)_7Si(CH_3)_2(CH_2)_9SiCl_3$
(11) $CH_3COO(CH_2)_{15}SiCl_3$
(12) $CH_3(CH_2)O_9SiCl_3$

Further, the chemicals shown in the following (21) to (44) including a hydrocarbon group could be used as the alkoxysilane-based adsorbent.

(21) $CF_3C_2O(CH_2)_{15}Si(OCH_3)_3$
(22) $CF_3(CH_2)_3Si(CH_3)_2(CH_2)_{15}Si(OCH_3)_3$
(23) $CF_3(CF_2)_5(CH_2)_2Si(CH_3)_2(CH_2)_9Si(OCH_3)_3$
(24) $CF_3(CF_2)_7(CH_2)_2Si(CH_3)_2(CH_2)_9Si(OCH_3)_3$
(25) $CF_3COO(CH_2)_{15}Si(OCH_3)_3$
(26) $CF_3(CF_2)_5(CH_2)_2Si(OCH_3)_3$
(27) $CH_3CH_2O(CH_2)_{15}Si(OCH_3)_3$
(28) $CH_3(CH_2)_3Si(CH_3)_2(CH_2)_{15}Si(OCH_3)_3$
(29) $CH_3(CH_2)_5Si(CH_3)_2(CH_2)_9Si(OCH_3)_3$
(30) $CH_3(CH_2)_7Si(CH_3)_2(CH_2)_9Si(OCH_3)_3$
(31) $CH_3COO(CH_2)_{15}Si(OCH_3)_3$
(32) $CH_3(CH_2)_9SiC(OCH_3)_3$
(33) $CF_3CH_2O(CH_2)_{15}Si(OC_2H_5)_3$
(34) $CF_3(CH_2)_3Si(CH_3)_2(CH_2)_{15}Si(OC_2H_5)_3$
(35) $CF_3(CF_2)_5(CH_2)_2Si(CH_3)_2(CH_2)_9Si(OC_2H_5)_3$
(36) $CF_3(CF_2)_7(CH_2)_2Si(CH_3)_2(CH_2)_9Si(OC_2H_5)_3$
(37) $CF_3COO(CH_2)_{15}Si(OC_2H_5)_3$
(38) $CF_3(CF_2)_5(CH_2)_2Si(OC_2H_5)_3$
(39) $CH_3CH_2O(CH_2)_{15}Si(OC_2H_5)_3$
(40) $CH_3(CH_2)_3Si(CH_3)_2(CH_2)_{15}Si(OC_2H_5)_3$
(41) $CH_3(CH_2)_5Si(CH_3)_2(CH_2)_9Si(OC_2H_5)_3$
(42) $CH_3(CH_2)_7Si(CH_3)_2(CH_2)_9Si(OC_2H_5)_3$
(43) $CH_3COO(CH_2)_{15}Si(OC_2H_5)_3$
(44) $CH_3(CH_2)_9SiC(OC_2H_5)_3$

In addition, in Example 1, as the silanol condensing catalyst, a metal carboxylate, a metal carboxylate ester, a metal carboxylate polymer, a metal carboxylate chelate, a titanic acid ester, a titanic acid ester chelate and the like can be used. More particularly, the followings can be used, that is, stannous acetic acid, dibutyltin dilaurate, dibutyltin dioctanoate, dibutyltin acetate, dioctyltin dilaurate, dioctyltin dioctanoate, dioctyltin diacetate, stannous octanoate, lead naphthenate, cobalt naphthenate, iron 2-ethylhexanoate, a dioctyltin bisoctylthioglycolate ester, a dioctyltin maleate ester, a dibutyltin maleate polymer, a dimethyltin mercapto propionate polymer, dibutyltin bisacetyl acetate, dioctyltin bisacetyl laurate, tetrabutyl titanate, tetranonyl titanate, and a bis(acetylacetonyl)dipropyl titanate.

Further, as a solvent of the film forming solution, an organic chlorine-based solvent not including aqueous, a hydrocarbon-based solvent, a fluorocarbon-based solvent, a silicone-based solvent, or a mixture of those can be used. In addition, when the solvent is evaporated so as to increase the particulate concentration without washing, it is preferable that a boiling point of the solvent is about 50 to 250 degree C.

More particularly, non-aqueous petroleum naphtha, solvent naphtha, petroleum benzine, petroleum ether, isoparaffin, normal paraffin, decalin, industrial gasoline, nonane, decane, kerosene, dimethylsilicone, phenylsilicone, alkyl-modified silicone, polyether silicone, and the like can be used. Further, when the adsorbent based on alkoxysilane is used, an alcohol-based solvent such as methanol, ethanol, or the like, or a solvent such as dimethylformamide or the like can be used in addition to the above-described solvents.

Further, as the fluorocarbon-based solvent, a chlorofluorocarbon-based solvent, Fluorinate (produced by 3M Corporation), Aflude (produced by Asahi Glass Co., Ltd.) and the like can be used. In addition, these solvent can be used independently, or can be used by mixing two or more kinds if these can be mixed. Further, the organic chlorine-based solvent such as chloroform can be added.

On the other hand, instead of the above-described silanol condensing solvent, when the ketimine compound, organic acid, the aldimine compound, the enamine compound, the oxazolidine compound, the aminoalkylalkoxy silane compound were used, the processing time could be shortened to about ½ to ⅔ although having the same concentration.

Further, when the silanol condensing catalyst was used by mixing with the ketimine compound, the organic acid, the aldimine compound, the enamine compound, the oxazolidine compound, or the aminoalkylalkoxy silane compound (although the mixing rate could be within the range of 1:9 to 9:1, the range of about 1:1 was ordinarily preferable), the processing time could be shortened several times further, and the time for forming the film could be shortened to one/several.

For example, when the process was carried out under the same conditions except the H3 which was the ketimine compound produced by Japan Epoxy Resin Corporation was used instead of the dibutyltin oxide which was the silanol catalyst, approximately similar results could be obtained except the reaction time could be shortened to about one hour.

Further, when the process was carried out under the same conditions except a mixture (having the mixing ratio of 1:1) of the H3 which was the ketimine compound produced by Japan Epoxy Resin Corporation and the dibutyltin bisacetyl acetonate which was the silanol catalyst was used, approximately similar results could be obtained except the reaction time could be shortened to about 20 minutes.

Therefore, it was clear that the ketimine compound, the organic acid, the aldimine compound, the enamine compound, the oxazolidine compound, and the aminoalkylalkoxy silane compound had higher activity than the silanol condensing catalyst.

Furthermore, when the silanol condensing catalyst was used by mixing with one of the ketimine compound, the organic acid, the aldimine compound, the enamine compound, the oxazolidine compound, and the aminoalkylalkoxy silane compound, the reactivity became further higher.

In addition, in this case, the ketimine compound used in the present invention was not limited especially. For example, the followings could be used, that is, 2,5,8-triaza-1,8-nonadien, 3,11-dimethyl-4,7,10-triaza-3,10-tridecadien, 2,10-dimethyl-3,6,9-triaza-2,9-undecadien, 2,4,12,14-tetramethyl-5,8,11-triaza-4,11-pentadecadien, 2,4,15,17-tetramethyl-5,8,11,14-tetraaza-4,14-octadecadien, 2,4,20,22-tetramethyl-5,12,19-triaza-4,19-trieicosadien, and the like.

Further, the organic acid used in the present invention was not limited especially. For example, formic acid, acetic acid, propionic acid, butyric acid, malonic acid or the like could be used, and approximately similar results could be obtained.

What is claimed is:

1. A biochemical chip, comprising:

a flow path including an inner surface having at least a portion that is covered with an arbitrary chemisorption monomolecular film as a surface layer having arbitrary surface energy, wherein the arbitrary chemisorption monomolecular film is formed with a mixed monomolecular film including at least a first monomolecular component having a terminal fluorocarbon group mixed with a second monomolecular component having a terminal hydrocarbon group, wherein the surface energy of the monomolecular film has an arbitrary value of about 2.6 mN/m.

2. The biochemical chip of claim 1, wherein the flow rate of a liquid in the flow path is controlled by varying the surface energy of the arbitrary chemisorption monomolecular film coating the flow path, wherein the mixed monomolecular film includes at least a first monomolecular component and a second monomolecular component, the first monomolecular component and a second monomolecular component having the following structures:

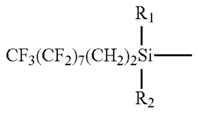

first monomolecular component; and

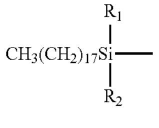

second monomolecular component;

wherein $R_1$ and $R_2$ are independently selected from Cl or $(OCH_3)$.

3. The biochemical chip according to claim 1 or 2, wherein the inner surface of the flow path is selectively covered with a chemisorption monomolecular film having a plurality of arbitrary surface energies.

4. The biochemical chip of claim 1 or 2, wherein the flow path is located within a chemical chip, an electrophoresis chip, a biochemical reactor, a biochemical fluidic system, or combination thereof.

5. The biochemical chip of claim 1 or 2, wherein the flow path has a cross-sectional dimension of from about 1 micron to about 5 microns.

6. A production method of a biochemical chip comprising:

a step of forming an arbitrary chemisorption monomolecular film as a surface layer having arbitrary surface energy on at least a portion of inner surfaces of flow path parts of first and second members which are processed to have flow paths, wherein at least a first monomolecular component includes a terminal fluorocarbon group and a second monomolecular component includes a terminal hydrocarbon group, the first and second molecular components are mixed and used so as to form the arbitrary chemisorption monomolecular film having the mixed first and second monomolecular components, wherein the surface energy of the monomolecular film has an arbitrary value of about 2.6 mN/m; and a step of facing and bonding the first and second members that have the monomolecular film.

7. The production method of a biochemical chip according to claim 6, comprising:

a step of contacting and reacting the first member and second member with a chemisorption liquid produced by mixing a non-aqueous organic solvent with a first chlorosilane compound containing the terminal fluorocarbon group and a second chlorosilane compound containing the terminal hydrocarbon group, and forming the first and second members having the arbitrary chemisorption monomolecular film containing the first monomolecular component having the terminal fluorocarbon group mixed with the second monomolecular component having the terminal hydrocarbon group; or a step of contacting and reacting the first member and second member with a chemisorption liquid produced by mixing a non-aqueous organic solvent with a first alkoxysilane compound containing the terminal fluorocarbon group and a second alkoxysilane compound containing the terminal hydrocarbon group, and forming the first and second members having the arbitrary chemisorption monomolecular film containing the first monomolecular component having the terminal fluorocarbon group mixed with the second monomolecular component having the terminal hydrocarbon group.

8. The method of claim 6, further comprising selectively forming resist films on the first and second members so as to define the flow paths.

9. The method of claim 6, wherein the mixed first and second monomolecular components have the following structures:

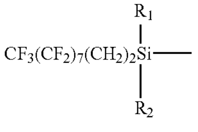

first monomolecular component; and

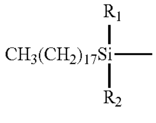

second monomolecular component;

wherein $R_1$ and $R_2$ are independently selected from Cl or $(OCH_3)$.

10. The method of claim 7, comprising forming the arbitrary chemisorption monomolecular film having the mixed first and second monomolecular components with a silanol condensing agent and one or more of a ketamine compound, organic acid, aldimine compound, enamine compound, oxazolidine compound, and/or aminoalkylalkoxy silane.

11. The method of claim 7, comprising forming the arbitrary chemisorption monomolecular film having the mixed first and second monomolecular components with one or more of a ketamine compound, organic acid, aldimine compound, enamine compound, oxazolidine compound, and/or aminoalkylalkoxy silane as the silanol condensing agent.

12. A biochemical chip, comprising:

two substrates coupled together and defining an internal fluid flow path;

an arbitrary chemisorption monomolecular film covering at least a portion of the internal fluid flow path as a surface layer having a surface energy about 2.6 mN/m, wherein the chemisorption monomolecular film includes:

at least a first monomolecular component having a terminal fluorocarbon group and a second monomolecular component having a terminal a hydrocarbon group.

13. The biochemical chip of claim 12, wherein the first and second monomolecular components have the following structures:

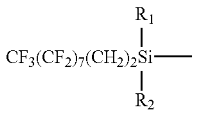

first monomolecular component; and

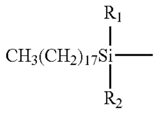

second monomolecular component;

wherein $R_1$ and $R_2$ are independently selected from Cl or $(OCH_3)$.

14. The biochemical chip of claim 12, wherein the chemisorption monomolecular film has a plurality of arbitrary surface energies.

15. A production method of a biochemical chip comprising:

a step of forming an arbitrary chemisorption monomolecular film as a surface layer having arbitrary surface energy on at least a portion of inner surfaces of flow path parts of first and second members which are processed to have flow paths, wherein the monomolecular film is formed with a silanol condensing agent and/or one or more of a ketamine compound, organic acid, aldimine compound, enamine compound, oxazolidine compound, and/or aminoalkylalkoxy silane, wherein at least a first monomolecular component includes a terminal fluorocarbon group and a second monomolecular component includes a terminal hydrocarbon group, the first and second molecular components are mixed and used so as to form the arbitrary chemisorption monomolecular film having the mixed first and second monomolecular components; and a step of facing and bonding the first and second members that have the monomolecular film.

16. The production method of a biochemical chip according to claim 15, comprising:

a step of contacting and reacting the first member and second member with a chemisorption liquid produced by mixing a non-aqueous organic solvent with a first chlorosilane compound containing the terminal fluorocarbon group and a second chlorosilane compound containing the terminal hydrocarbon group, and forming the first and second members having the arbitrary chemisorption monomolecular film containing the first monomolecular component having the terminal fluorocarbon group mixed with the second monomolecular component having the terminal hydrocarbon group; or a step of contacting and reacting the first member and second member with a chemisorption liquid produced by mixing a non-aqueous organic solvent with a first alkoxysilane compound containing the terminal fluorocarbon group and a second alkoxysilane compound containing the terminal hydrocarbon group, and forming the first and second members having the arbitrary chemisorption monomolecular film containing the first monomolecular component having the terminal fluorocarbon group mixed with the second monomolecular component having the terminal hydrocarbon group.

17. The method of claim 15, comprising preparing the monomolecular film to have a surface energy with an arbitrary value of about 2.6 mN/m.

* * * * *